US011826138B2

(12) United States Patent
Tan et al.

(10) Patent No.: US 11,826,138 B2
(45) Date of Patent: *Nov. 28, 2023

(54) EAR-WORN DEVICES WITH DEEP BREATHING ASSISTANCE

(71) Applicant: STARKEY LABORATORIES, INC., Eden Prairie, MN (US)

(72) Inventors: Christine Marie Tan, Eden Prairie, MN (US); Christophe Daniel Micheyl, Saint Genis Laval (FR)

(73) Assignee: STARKEY LABORATORIES, INC., Eden Prairie, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/073,069

(22) Filed: Dec. 1, 2022

(65) Prior Publication Data

US 2023/0093747 A1  Mar. 23, 2023

Related U.S. Application Data

(63) Continuation of application No. 16/027,903, filed on Jul. 5, 2018, now Pat. No. 11,540,743.

(51) Int. Cl.
*A61B 5/08* (2006.01)
*A61B 5/113* (2006.01)
(Continued)

(52) U.S. Cl.
CPC ............ *A61B 5/0816* (2013.01); *A61B 5/113* (2013.01); *A61B 5/6815* (2013.01);
(Continued)

(58) Field of Classification Search
CPC .............. A61B 5/08; A61B 5/113; A61B 5/00
See application file for complete search history.

(56) References Cited

U.S. PATENT DOCUMENTS 6,305,943 B1  10/2001  Pougatchev et al.
6,955,542 B2  10/2005  Roncalez et al.
(Continued)

FOREIGN PATENT DOCUMENTS

DE  102011107247  9/2001
EP  3154278  4/2017
WO  2014/010165  1/2014

OTHER PUBLICATIONS

Abushakra and Faezipour, "Acoustic Signal Classification of Breathing Movements to Virtually Aid Breath Regulation," IEEE Journal of Biomedical and Health Informatics, Mar. 2013, 17(2):493-500.
(Continued)

*Primary Examiner* — Eddy Saint-Vil
(74) *Attorney, Agent, or Firm* — Mueting Raasch Group

(57) ABSTRACT

A method for guiding deep breathing may include receiving a request from a user to initiate a deep breathing exercise on a user-controlled device. The method may include monitoring deep breathing using one or more sensors on an ear-worn device in response to initiating the deep breathing exercise. Examples of sensors include at least one of a motion detector, a microphone, a heart rate sensor, and an electrophysiological sensor. The method may further include initiating an end to the deep breathing exercise. The method may be used with various hearing systems including an ear-worn device and optionally a user-controllable device, such as a smartphone.

24 Claims, 11 Drawing Sheets

(51) Int. Cl.
*A61B 5/00* (2006.01)
*A61B 5/0205* (2006.01)

(52) U.S. Cl.
CPC .......... *A61B 5/7267* (2013.01); *A61B 5/0205* (2013.01); *A61B 5/4815* (2013.01); *A61B 5/6803* (2013.01); *A61B 5/6898* (2013.01); *A61B 5/7214* (2013.01); *A61B 2562/0204* (2013.01); *A61B 2562/0219* (2013.01); *A61M 2230/42* (2013.01)

(56) References Cited

U.S. PATENT DOCUMENTS

| | | | |
|---|---|---|---|
| 7,252,640 | B2 | 8/2007 | Ni et al. |
| 7,267,652 | B2 | 9/2007 | Coyle et al. |
| 7,510,531 | B2 | 3/2009 | Lee et al. |
| 8,888,700 | B2 | 11/2014 | Banet et al. |
| 8,972,197 | B2 | 3/2015 | Jangle et al. |
| 9,744,330 | B2 | 8/2017 | Searchfield et al. |
| 9,779,751 | B2 | 10/2017 | Bikko |
| 9,830,832 | B2 | 11/2017 | Warren et al. |
| 10,219,740 | B2 | 3/2019 | Warren et al. |
| 10,582,908 | B2 | 3/2020 | Stroman |
| 10,617,842 | B2 | 4/2020 | Espi Maques et al. |
| 2008/0015457 | A1 | 1/2008 | Silva |
| 2009/0263773 | A1 | 10/2009 | Kotlyar et al. |
| 2010/0041965 | A1* | 2/2010 | Kang .................. A61B 5/00 600/301 |
| 2010/0130873 | A1* | 5/2010 | Yuen ................... A61B 5/113 600/595 |
| 2013/0053718 | A1 | 2/2013 | Hung et al. |
| 2017/0172459 | A1 | 6/2017 | Bernstein et al. |
| 2017/0258329 | A1 | 9/2017 | Marsh |
| 2018/0014741 | A1 | 1/2018 | Chou |
| 2018/0020937 | A1 | 1/2018 | Chou |
| 2018/0122509 | A1 | 5/2018 | Christiansson |
| 2018/0296877 | A1 | 10/2018 | Reeh et al. |
| 2018/0310855 | A1 | 11/2018 | Connor |
| 2019/0029563 | A1 | 1/2019 | Sels et al. |
| 2019/0038179 | A1 | 2/2019 | Tanriover et al. |

OTHER PUBLICATIONS

EP Search Report for 19184804.3 dated Oct. 9, 2019, 17 pages.
European Office Action from EP Application No. 19184804.3 dated Oct. 29, 2020, 17 pages.
Hartmann, Signals, Sound, and Sensation. American Institute of Physics, Woodbury, N.Y, 1997. Cover Page, Summary, and Table of Contents. 3 pages.
Jarne, "Simple empirical algorithm to obtain signal envelope in three steps," Mar. 20, 2017, published online by arXiv. Cited as: arXiv: 1703.06812v1. Available on the internet URL:https://ia801506.us.archive.org/1/items/arxiv-1703.06812/1703.06812.pdf; 10 pages.
Office Action from EP Application No. 19184804.3 dated Mar. 4, 2020, 17 pages.
Potamianos and Maragos, "A Comparison of the Energy Operator and the Hilbert Transform Approach to Signal and Speech Demodulation," Signal Processing, May 1994; 37(1):95-120.
Schloss, "On the Automatic Transcription of Percussive Music—From Acoustic Signal to High-Level Analysis," Thesis, 1985, Stanford University; 126 pages.
Yahya and Faezipour, "Automatic Detection and Classification of Acoustic Breathing Cycles," Presented at the 2014 Zone 1 Conference of the American Society for Engineering Education, Apr. 3-5, 2014, Bridgeport, Connecticut, USA. Published in Proceedings of the 2014 Zone 1 Conference of the American Society for Engineering Education, May 2014; 6 pages.

* cited by examiner

EAR-WORN DEVICES WITH DEEP BREATHING ASSISTANCE

CROSS-REFERENCE TO RELATED APPLICATIONS

This application is a continuation application of U.S. application Ser. No. 16/027,903, filed Jul. 5, 2018, the disclosure of which is incorporated by reference herein in its entirety.

TECHNICAL FIELD

The present disclosure relates generally to ear-worn devices and in particular to hearing assistance devices with functionality to assist a wearer with an activity other than hearing.

BACKGROUND

Hearing assistance devices, such as hearing aids, may be used to assist wearers suffering hearing loss by transmitting amplified sounds to one or both ear canals. Such devices typically include hearing assistance components such as a microphone for receiving ambient sound, an amplifier for amplifying the microphone signal in a manner that depends upon the frequency and amplitude of the microphone signal, a speaker or receiver for converting the amplified microphone signal to sound for the wearer, and a battery for powering the components.

In certain types of hearing aids, the hearing assistance components are enclosed by a housing that is designed to be worn in the ear for both aesthetic and functional reasons.

SUMMARY

In one aspect, the present disclosure relates to a method for guiding deep breathing. The method includes receiving a request from a user to initiate a deep breathing exercise on a user-controlled device; monitoring deep breathing using one or more sensors on an ear-worn device in response to initiating the deep breathing exercise, wherein the one or more sensors include at least one of a motion detector, a microphone, a heart rate sensor, and an electrophysiological sensor; and initiating an end to the deep breathing exercise.

In one aspect, the present disclosure relates to an ear-worn device. The device includes a housing configured to be worn by a user in or proximate to an ear of the user; a motion detector contained in the housing and configured to monitor user motion; a microphone contained in the housing and configured to monitor ambient sound; a communication interface contained in the housing and configured to communicate with a user-controlled device; a controller including a processor contained in the housing and operably coupled to the motion detector, the microphone, and the communication interface. The controller is configured to: receive a request to initiate a deep breathing exercise from the user-controlled device; monitor user motion and ambient sound in response to receiving the request; and provide monitored breathing data based on at least the monitored user motion.

In one aspect, the present disclosure relates to a user-controllable device. The user-controllable device includes: a user interface having a display and configured to receive user input; a communication interface configured to connect to an ear-worn device; a controller including a processor operably coupled to the user interface and the communication interface. The controller is configured to: receive a request to initiate a deep breathing exercise based on user input at the user interface; connect to the ear-worn device to receive monitored breathing data based on user motion and optionally monitored ambient sound; and initiate an end to the deep breathing exercise.

In one or more aspects, a method or configuration includes: determining whether a breathing pattern is detectable in an ambient acoustic environment using a microphone of the ear-worn device or of the user-controlled device; and monitoring deep breathing using a motion detector and the microphone of the ear-worn device or of the user-controlled device in response to the breathing pattern being detectable.

In one or more aspects, a method or configuration includes initiating an end to the deep breathing exercise after a predetermined period of time, in response to wearer input, or in response to achieving a deep breathing goal.

In one or more aspects, a method or configuration includes calibrating the motion detector using a pre-determined baseline condition.

In one or more aspects, a method or configuration includes logging deep breathing data based on the monitored deep breathing over time; and providing progress data based on the logged deep breathing data to the user with the user-controlled device or the ear-worn device.

In one or more aspects, the progress data provided to the user includes at least one of: results of a comparison of the deep breathing data to a deep breathing goal; merit badges received; and reminders to perform deep breathing exercises.

In one or more aspects, a method or configuration includes providing deep breathing guidance during the deep breathing exercise to the user with the user-controlled device or the ear-worn device.

In one or more aspects, breathing rate guidance provided to the user is based on a breathing rate goal.

In one or more aspects, content of the deep breathing guidance is based on whether an inhalation, an exhalation, or a holding of the breath is detected.

In one or more aspects, a method or configuration includes providing a masking noise for tinnitus during at least part of the deep breathing exercise.

In one or more aspects, a method or configuration includes modifying the masking noise in response to a detected breathing pattern.

In one or more aspects, at least one parameter of the masking noise modified in response to the detected breathing pattern includes at least one of: a sound level, a frequency response, a modulation rate for amplitude, a modulation rate for frequency, and a type of masking noise.

In one or more aspects, a method or configuration includes: determining whether a breathing pattern is detectable in an ambient acoustic environment using the microphone of the ear-worn device or a microphone of the user-controlled device; and providing monitored breathing data based on the monitored user motion and monitored ambient sound in response to the breathing pattern being detectable.

In one or more aspects, a method or configuration includes: providing monitored breathing data without using monitored ambient sound in response to the breathing pattern not being detectable.

In one or more aspects, the motion detector includes at least one of an accelerometer and a gyroscope.

In one or more aspects, at least one of a heart rate sensor and an electrophysiological sensor are included.

In one or more aspects, a method or configuration includes storing progress data based on the monitored breathing data.

In one or more aspects, the communication interface is configured to connect to the internet to share progress data with others.

In one or more aspects, a method or configuration includes commanding the user interface to display at least one of: a measured breathing rate; a breathing rate goal; guidance through the monitored deep breathing; and instructions for calibrating the ear-worn device.

In one or more aspects, a method or configuration includes receiving user input from the user interface including at least one of: a breathing exercise duration; a breathing rate starting goal; and a breathing rate end goal.

In one or more aspects, a method or configuration includes modifying at least one parameter for a masking noise in response to a detected breathing pattern.

BRIEF DESCRIPTION OF THE DRAWINGS

Various embodiments of the present disclosure are described below in the detailed description with reference to the following drawings.

DETAILED DESCRIPTION

Figure 1:
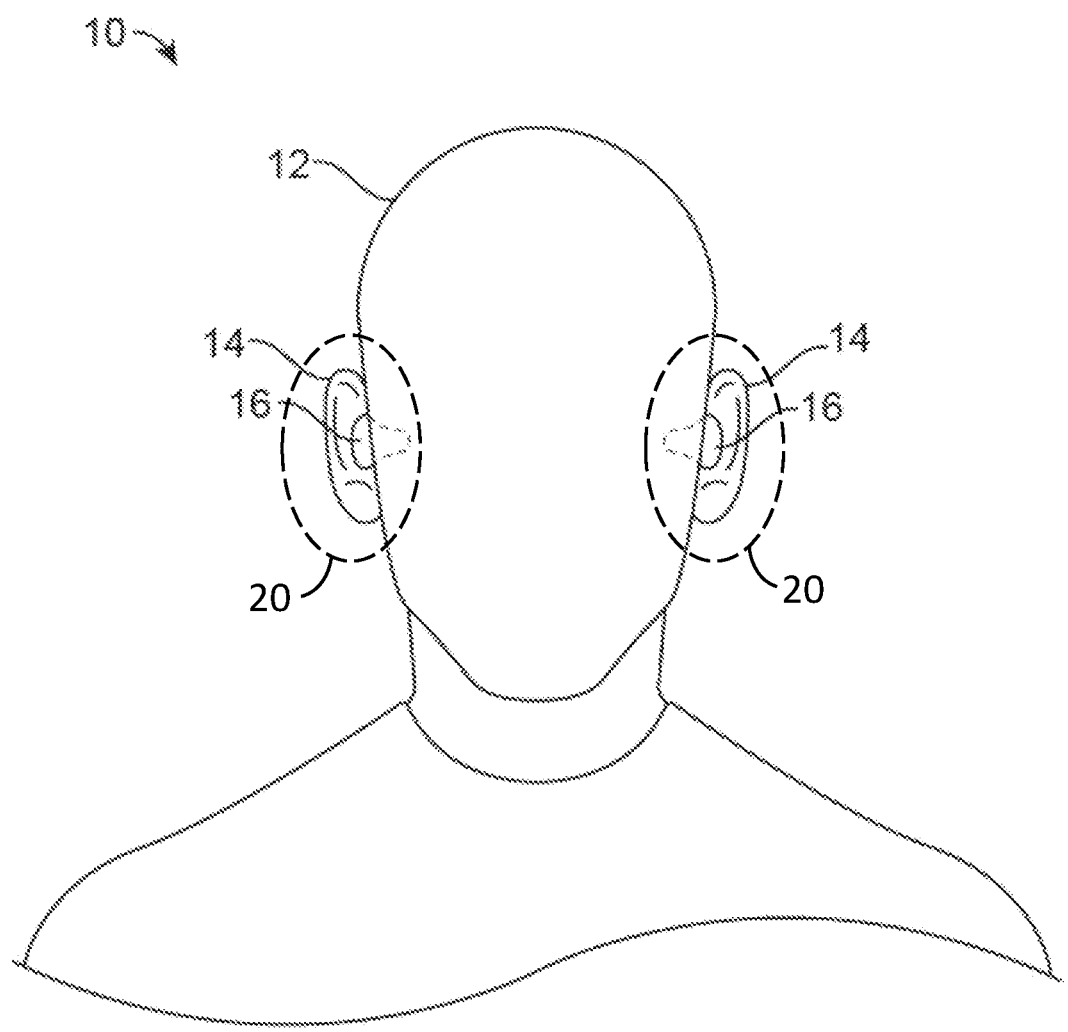
FIG. 1 shows a hearing system including ear-worn devices according to various embodiments of the present disclosure.

The present disclosure relates to an ear-worn device with functionality to assist a wearer with an activity other than hearing. Although reference is made herein to hearing assistance devices, such as a hearing aid, deep breathing assistance functionality may be used with any ear-worn device. Non-limiting examples of ear-worn devices with various functionality include: hearing assistance devices, hearable devices (for example, wired or wireless earbuds, Bluetooth® headsets, or back-vented vented tweeter-woofer devices), wearables or health monitors (for example, step counter or heart rate monitor), or other portable or personal electronics (for example, smartwatch or smartphone). Various other applications will become apparent to one of ordinary skill in the art having the benefit of the present disclosure.

A hearing device may include hearing assistance devices, or hearing aids of various types, such as behind-the-ear (BTE), in-the-ear (ITE), in-the-canal (ITC), receiver-in-canal (RIC), completely-in-the-canal (CIC), or invisible-in-the-canal (IIC)-type hearing aids. It is understood that BTE type hearing aids may include devices that reside substantially behind the ear or over the ear. Such devices may include hearing aids with receivers associated with the electronics portion of the device, or hearing aids of the type having receivers in the ear canal of the user, including but not limited to receiver-in-canal (RIC) or receiver-in-the-ear (RITE) designs. The present subject matter can also be used in hearing assistance devices generally, such as cochlear implant type hearing devices and such as deep insertion devices having a transducer, such as a receiver or microphone, whether custom fitted, standard, open fitted, or occlusive fitted. The present subject matter may additionally be used in consumer electronic wearable audio devices having various functionalities. It is understood that other devices not expressly stated herein may also be used in conjunction with the present subject matter.

Hearing assistance devices are typically small to facilitate comfort. It may be beneficial to provide a hearing assistance device with functionality to assist the wearer with various activities, particularly for activities that a wearer of a hearing assistance device may regularly engage in, such as deep breathing exercises. It may also be beneficial to provide the wearer with a coordinated user interface using the hearing assistance device and another user-controllable device, such as a smartwatch, smartphone, or tablet. Further, it may be beneficial to track and monitor various health information for the wearer.

Deep breathing exercises involve the regulation of controlled inhaled and exhaled breaths for relaxation, stress reduction, and pain management. In audiology, deep breathing exercises may be helpful for people with tinnitus who have comorbidities of anxiety, depression, sleep disorders, and stress. One Progressive Tinnitus Management (PTM) scheme, for example, promotes various relaxation techniques including deep breathing exercises for persons with tinnitus. It may be beneficial to have monitoring and guidance during deep breathing exercises instead of relying upon wearers to monitor their own abilities. It may also be beneficial to provide real-time feedback to help improve breathing techniques or to better guide the breathing task.

Some devices have been developed to facilitate deep breathing exercises that require the user to carry an additional accessory, such as a chest monitor. It may be beneficial for hearing assistance device wearers to have deep breathing exercise assistance without wearing an additional accessory that must be separately carried and recharged.

This disclosure provides ear-worn devices with deep breathing assistance. In particular, the ear-worn device has deep breathing detection functionality, which may be used to assist a wearer, or user, with deep breathing exercise sessions. The ear-worn device may leverage the use of motion detection sensors alone, or in combination with other components (e.g., microphones), to detect breaths during deep breathing exercise sessions. Breath detection during the session may be used to provide guidance and feedback to the wearer to modulate their breathing during the task, for example, with audio queues (e.g., verbal feedback) or with modulated audio heard during the session. The ear-worn device may be connected to another user-controllable device, such as a smartphone, to provide breathing detection functionality with a coordinated user interface. The coordinated user interface may provide feedback on breathing techniques during the session.

Advantageously, an ear-worn device with deep breathing assistance may provide a single, integrated system for wearers of hearing assistance devices who may have hearing loss or tinnitus and may benefit from carrying out deep breathing exercises. Using this system, the hearing device wearer may avoid carrying or wearing additional accessories for deep breathing guidance. Further, integration of the deep breathing exercises with an ear-worn device and optionally another user-controllable device may facilitate improvements in the exercises and better results (e.g., reduced heart rate or tinnitus relief) when those exercises are modified or assisted using the ear-worn device.

All scientific and technical terms used herein have meanings commonly used in the art unless otherwise specified. The definitions provided herein are to facilitate understanding of certain terms used frequently herein and are not meant to limit the scope of the present disclosure.

As used herein, the term "ear-worn device" or "ear-level device" refers to an electronic device worn in or around an ear of the wearer. For example, the ear-worn device may be hooked on the pinna (e.g., using a BTE hearing aid) or worn in the ear canal (e.g., using an ITC hearing aid). Ear-worn devices may include devices that are worn proximate, or adjacent, to the ear. Ear-worn devices may exclude, for example, devices worn around the eyes of a user or on a headband or neckband.

As used herein, the term "hearing device" refers to a device that provides sound that is heard by the user. One type of hearing device is a hearing assistance device, which may help a user to hear sounds in the ambient environment. Typically, hearing devices are ear-worn devices.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows hearing system 10 that may include one or more ear-worn devices 16. Ear-worn device 16 may be a hearing device including a hearing aid, an earphone, or a headphone (e.g., earbud). Each ear-worn device 16 may include one or more sensors, such as an integrated motion detector, a microphone, a heart rate sensor, or an electrophysiological sensor, that may be used individually or in combination to detect deep breaths. Deep breath detection may be used to provide feedback to wearer 12 during, for example, deep breathing exercises.

As illustrated, each ear-worn device 16 may be worn proximate, or adjacent to, the pinna or worn in one or both ears 14 of wearer 12. As illustrated, each ear-worn device 16 is positioned, at least partially, in each ear 14.

In some embodiments, each ear-worn device 16 is positioned in a region or zone 20 around each ear 14. In particular, each sensor, such as a motion detector or microphone, of ear-worn device 16 may be positioned within zone 20. Various embodiments of ear-worn device 16 of hearing system 10 may not include sensors, such as a motion detector or microphone, outside of zone 20 or positioned away from the ears 14 of wearer 12, such as sensors positioned on headbands going over the head, on neckbands behind the head, or on cords connected to other devices.

Figure 2:
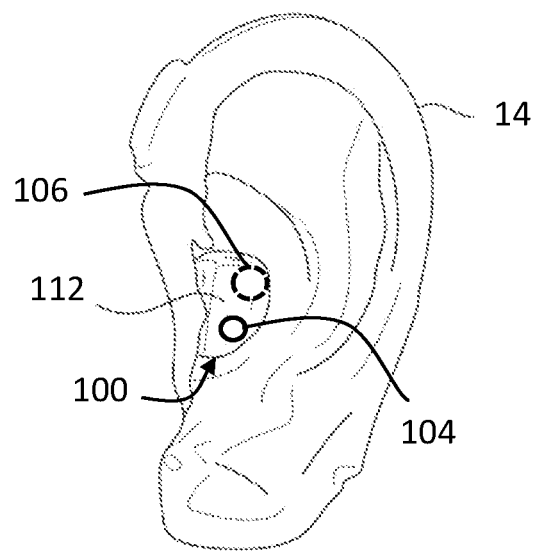
FIG. 2 shows one type of ear-worn device that may be used with the hearing system of FIG. 1.
Figure 3:
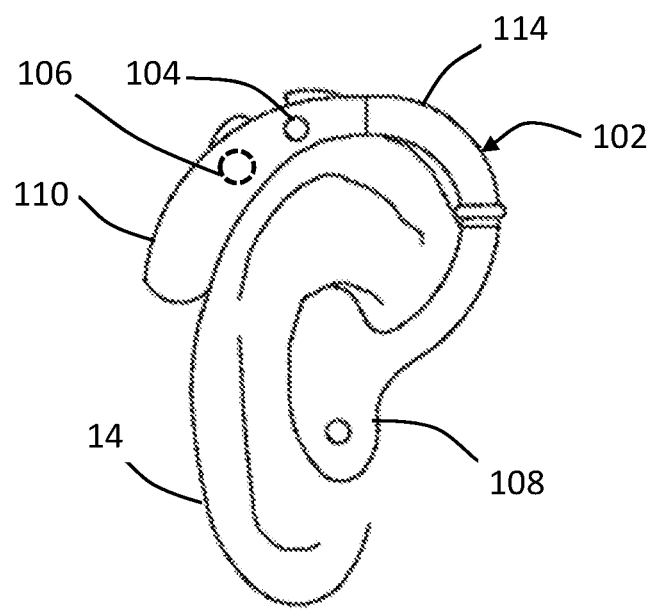
FIG. 3 shows another type of ear-worn device that may be used with the hearing system of FIG. 1.

FIGS. 2 and 3 show two different types of ear-worn hearing devices 100, 102 that may be used in hearing system 10. FIG. 2 shows ITE device 100, and FIG. 3 shows BTE device 102 worn in or around the pinna of ear 14. Device 102 may include earpiece 108 positioned in ear 14 and ear hook 110 positioned outside and behind ear 14. In addition to hearing assistance, for example, each device 100, 102 is configured to facilitate deep breathing exercises. In particular, each device 100, 102 includes at least one microphone 104 and at least one motion detector 106. Housing 112 may be worn in the ear, and part of housing 114 may be worn proximate to the ear.

Microphone 104 and motion detector 106 may each be contained within a housing 112, 114 of the respective device 100, 102. In general, motion detector 106 is configured to monitor user motion. In general, microphone 104 configured to monitor ambient sound. Microphone 104 may be described as an onboard microphone.

Microphone 104 may be used in conjunction with motion detector 106 to further improve the detection of breathing during the deep breathing exercises. For example, motion detector 106 may be used to detect movement of the user's ear 14 in response to deep breathing, and microphone 104 may be used to detect vocalized and non-vocalized sounds generated during inhalation and exhalation, which described herein in more detail.

One or more components, such as controllers, motion detectors, microphones, speakers, or other sensors, described herein may include a processor, such as a central processing unit (CPU), computer, logic array, or other device capable of directing data coming into or out of an ear-worn hearing device or user-controllable device. The controller may include one or more computing devices having memory, processing, and communication hardware. The controller may include circuitry used to couple various components of the controller together or with other components operably coupled to the controller. The functions of the controller may be performed by hardware and/or as computer instructions on a non-transient computer readable storage medium.

The processor of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller may utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

Figure 4:
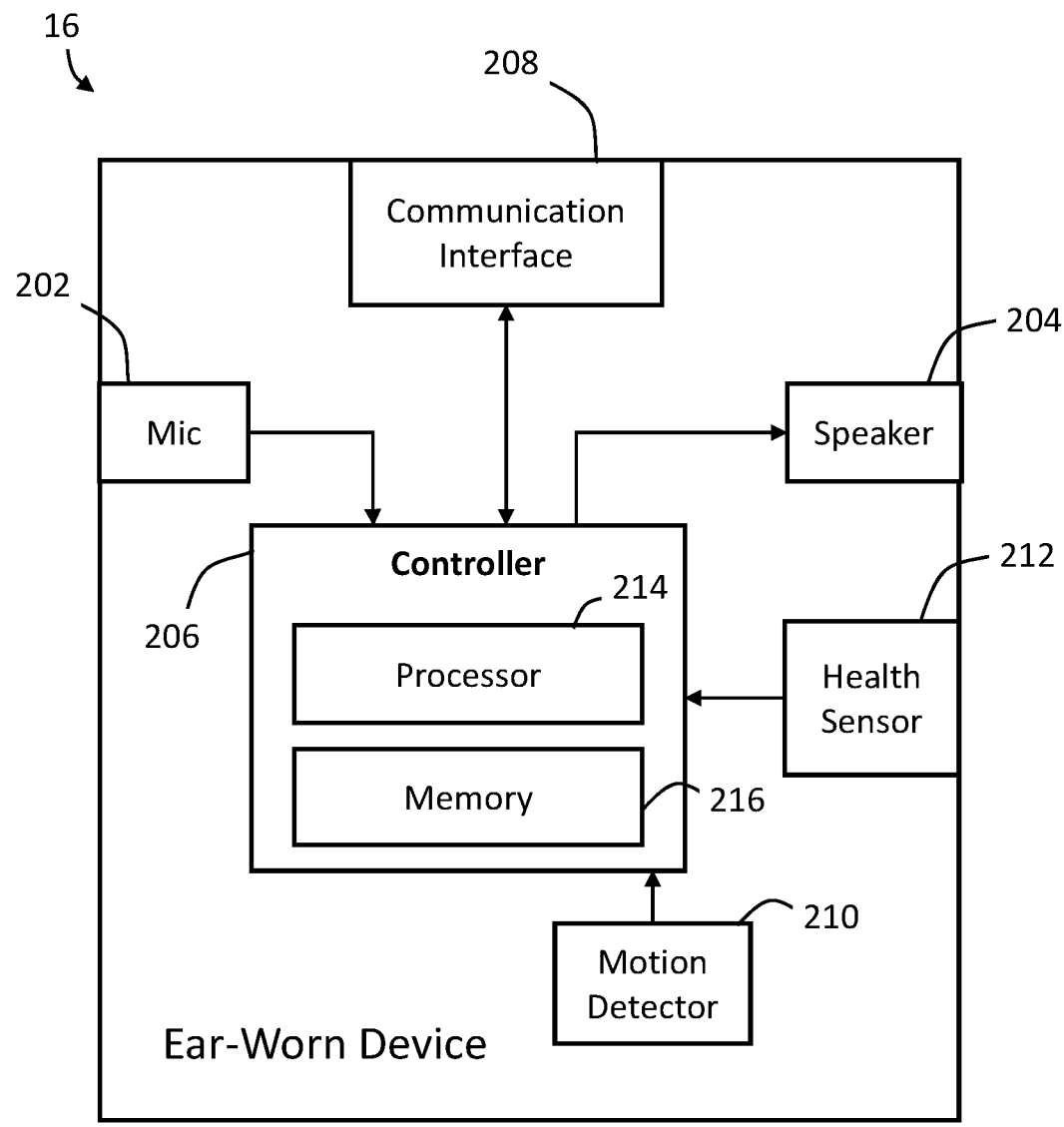
FIG. 4 shows a layout of one of the ear-worn devices of FIGS. 1-3.

FIG. 4 shows one example layout of ear-worn device 16. Ear-worn device 16 may include electronic components disposed within a housing. The electronic components may be disposed in any suitable location or arrangement within the housing. The electronic components may include any suitable device or devices, e.g., integrated circuits, power sources, microphones, receivers, etc. For example, in one or more embodiments, the components include one or more of a controller, a microphone, a receiver (e.g., speaker), a power source, an antenna (e.g., of a communication interface), or various other sensors (e.g., motion detector, heart rate sensor, or electrophysiological sensor). The microphone, receiver, power source, antenna, and any additional sensors may be electrically connected to the controller using any suitable technique or techniques. In the illustrated embodiment, ear-worn device 16 includes microphone 202, speaker 204, controller 206, communication interface 208, motion detector 210, and health sensor 212.

Microphone 202 may be electrically connected to the controller 206. Although one microphone 202 is depicted, the components may include any suitable number of microphones. In one or more embodiments, a port or opening may be formed in the housing, and the microphone may be disposed adjacent the port to receive audio information from the wearer's ambient acoustic environment. In one or more embodiments, microphone 202 is selected to detect one or more audio signals and convert such signals to an electrical signal that is provided to processor 214 of controller 206. Controller 206 may include an analog-to-digital convertor (not shown) that converts the electrical signal from microphone 202 to a digital signal.

Speaker 204 may be electrically connected to controller 206. Speaker 204 may also be referred to as a receiver. In one or more embodiments, speaker 204 is adapted to convert an electrical signal from controller 206 to an acoustic output or sound that may be transmitted from the housing to the wearer. For example, in hearing applications, speaker 204 may be an amplified version of an audio signal received from microphone 202.

A power source (not shown) may be electrically connected to controller 206 and may be adapted to provide electrical energy to the controller and one or more of the other components. The power source may include any suitable power source or power sources, e.g., a battery. In one or more embodiments, the power source may include a rechargeable battery. In one or more embodiments, the components may include two or more power sources.

Controller 206 may be contained within a housing of ear-worn device 16. Controller 206 may be operably coupled to motion detector 210, microphone 202, and communication interface 208. In some embodiments, controller 206 is configured to receive a request to initiate a deep breathing exercise from a user-controlled device. Controller 206 may be configured to monitor user motion and ambient sound in response to receiving the request. Further, controller 206 may be configured to provide monitored breathing data based on at least the monitored user motion. In embodiments where ear-worn device 16 is utilized as a hearing aid, controller 206 may be adapted to employ programmable gains to adjust the hearing device output to the wearer's particular hearing impairment.

In the illustrated embodiment, controller 206 includes processor 214 and memory 216. In some embodiments, controller 206 may include a digital signal processor (DSP), microprocessor, microcontroller, other digital logic, or combinations of these. Processing may be done by a single processor or may be distributed over different devices. For example, the processing of signals may be performed using controller 206 or over different devices. Processing may be done in the digital domain, the analog domain, or combinations thereof. In some embodiments, processing may be done using subband processing techniques. Processing may be done using frequency domain or time domain approaches. Some processing may involve both frequency and time domain aspects. For brevity, in some examples drawings may omit certain blocks that perform frequency synthesis, frequency analysis, analog-to-digital conversion, digital-to-analog conversion, amplification, buffering, and certain types of filtering and processing. In one or more embodiments, processor 214 or other processing devices execute instructions to perform a number of signal processing tasks. Such embodiments may include analog components in communication with processor 214 to perform signal processing tasks, such as sound reception by microphone 202 or playing of sound using speaker 204.

Ear-worn device 16 may be configured to communicate by wire or wirelessly with each other or other devices. Processor 214 may be configured to control communication to and from ear-worn device 16 through communication interface 208. Communication interface 208 may be used to communicate information, for example, audio streaming data or control signals, to or from one or more other devices. Communication interface 208 may be contained in a housing of ear-worn device 16. In general, communication interface 208 is configured to communicate with a user-controlled device.

In some embodiments, communication interface 208 may include a transceiver. The transceiver may include a receiver portion that receives communication signals from an antenna structure, demodulates the communication signals, and transfers the signals to controller 206 for further processing. The transceiver may also include a transmitter portion that modulates output signals from controller 206 for transmission via the antenna structure. Electrical signals from microphone 202 and wireless communication signals received via communication interface 208 may be processed by controller 206 and converted to acoustic signals played to the user via speaker 204. In some embodiments, communication interface 208 may include a wired connection, such as an audio adapter or a wired data connection.

The antenna structure of communication interface 208 may include one or more antennas having any suitable configuration. For example, antenna configurations may vary and may be included within the housing or be external to the housing. Further, the antenna structure may be compatible with any suitable protocol or combination of protocols.

For example, in one or more embodiments, ear-worn device 16 may be connected to one or more external devices using, e.g., Bluetooth®, Wi-Fi, magnetic induction, etc. For example, in one or more embodiments, ear-worn device 16 may be wirelessly connected to the internet using any suitable technique or techniques. Such connection may enable ear-worn device 16 to access any suitable databases, including medical records databases, cloud computing databases, personal databases, or social networks.

Motion detector 210 may be electrically connected to controller 206. Motion detector 210 may include any suitable type of motion detector, such as one or more of an accelerometer, a gyroscope, a magnetometer, or other inertial measurement unit (IMU). Motion detector 210 may be contained within ear-worn device 16. In some embodiments, motion detector 210 may be calibrated. In some embodiments, motion detector 210 may be calibrated to a predetermined baseline condition.

In embodiments where ear-worn device 16 includes a second hearing device disposed on an opposite side of the wearer's head, communication interface 208 may be utilized to communicate with a communication interface of the second hearing device. In one or more embodiments, a low-power link across the wearer's head may be utilized to transmit electromagnetic signals between the first and second hearing devices. Sensor data from the one or more sensors may be coordinated between the two hearing devices. For example, an accelerometer and a microphone disposed in each device may be utilized to determine deep breathing patterns based on signals from both devices.

One or more sensors of ear-worn device 16 may also be utilized to electrically connect to the wearer's body such that the body may be utilized as an antenna for transmitting information to and from the hearing device. Such sensors may be considered part of communication interface 208. One or more sensors may electrically connect ear-worn device 16 to one or more additional body-worn devices by sending electromagnetic signals between the devices through the body. For example, for hearing systems that include two hearing devices, one or more sensors may be utilized for communication between the hearing devices through the skull of the wearer, i.e., ear-to-ear communications. Such communication may be utilized to send electromagnetic signals from one device to the other. For example, the wearer may adjust a volume of an acoustic signal provided by the hearing devices by changing the volume on one device, which sends a control signal to the other device that adjusts its volume.

Ear-worn device 16 may be used to detect breathing patterns, particularly deep breathing patterns, using microphone 202. For example, a breathing rate may be detected. In some embodiments, acoustic detection of breathing patterns may be performed using existing signal-processing algorithms. Algorithms used may operate on pre-defined spectral, temporal features, or both of the microphone signal. For example, an algorithm may operate on low-frequency spectral features that are characteristic of breathing noises, which may be used in combination with temporal-modulation filtering.

Alternatively, or additionally, relevant features of signals from microphone 202 for the detection and/or the discrimination of breathing patterns in a given individual, or a group of individuals, may be learned by an algorithm using machine-learning techniques, such as Gaussian mixture model or support vector machines. The information provided by acoustic detection may add to, or enhance, the information provided by motion detection sensor 210.

In some embodiments, signals from motion detector 210 or microphone 202 may be combined with, or compared to, sensor signals conveying information about heart rate. For example, health sensor 212 may include a heart rate sensor, or heart rate monitor. Heart rate may be influenced, or modulated, by breathing and may provide additional information on the wearer's current state of relaxation. A heart rate sensor may be located on ear-worn device 16 (e.g., inside the ear canal) or on another part of the body (e.g., on the chest). In the latter case, heart rate information may be sent to and received by communication interface 208 of ear-worn device 16, or to a different user-controllable device (e.g., smartphone) with which device 16 may communicate using communication interface 208.

In some embodiments, electrophysiological information may be used in combination, or compared with signals from motion detector 210 or microphone 202. For example, health sensor 212 may include an electrophysiological sensor. Health sensor 212 may be operatively connected to controller 206. An electrophysiological sensor may be located in or around the ear, or from other locations on the body, and used to infer state of relaxation, in order to provide additional feedback to modulate breathing during the session.

Health sensor 212 may include any suitable sensor or sensors to monitor various health parameters of the wearer. Health sensor 212 may include any suitable type of sensor to monitor various health parameters, such as one or more of: an electrical sensor, an optical sensor, a bioelectrical sensor including biological sensors, and a bioactive sensor. Non-limiting examples of suitable health sensors 212 include one or more of: heart rate sensor, blood pressure sensor, magnetometer, electrooculography (EOG) sensor, electroencephalography (EEG) sensor, amperometric sensor, blood sugar sensor, light sensor, body temperature sensor, galvanic skin response (GSR) sensor, and combinations thereof. Health sensor 212 may be adapted to detect any suitable physiological characteristic of the wearer. For example, the physiological characteristic may include at least one of body position, eye movement, body temperature, heart rate, EEG, skin impedance, and combinations thereof. An electrophysiological sensor may be used to detect one or more of these physiological characteristics.

Figure 5:
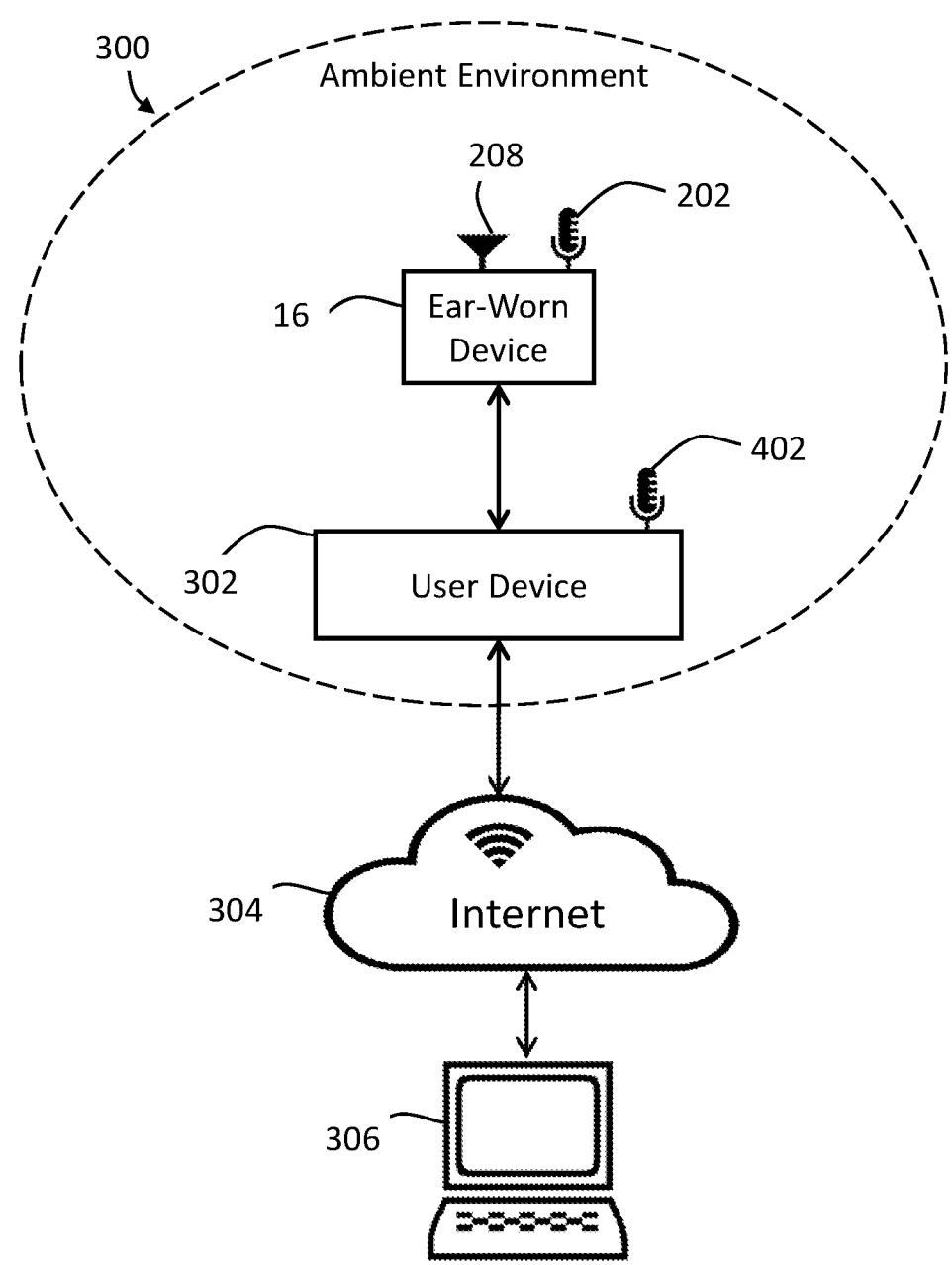
FIG. 5 shows the ear-worn device of FIG. 1 used in an ambient acoustic environment with a user-controllable device.

FIG. 5 shows one example of an integrated system for using ear-worn device 16 in an ambient environment 300 with user-controllable device 302. Non-limiting examples of user-controllable device 302 include a mobile phone (e.g., smartphone), tablet, smartwatch, or software application running on a portable user-controllable device (e.g., laptop). As illustrated, ear-worn device 16 is in operative communication with user-controllable device 302. User-controllable device 302 may be in operative communication with remote computer 306 (e.g., a server, a personal computer, or a friend's smartphone) over the internet 304. As illustrated, ear-worn device 16 includes microphone 202 and communication interface 208, and user-controllable device 302 includes microphone 402. Each of ear-worn device 16 and user-controllable device 302 may include various other sensors not shown in this illustration.

User-controllable device 302 may be configured to modulate the deep breathing exercise according to the feedback provided by ear-worn device 16. For instance, an application running on user-controllable device 302 may stream, or provide, instructions to the wearer to better modulate breathing, provide visual indicators, or custom tailor the instructions based on the ability of the wearer.

Accuracy of breath detection may be improved, for example, by leveraging information provided by a pair of ear-worn devices 16 in cases where the wearer has one ear-worn device 16 on each ear. A statistical technique or cross correlation may be applied to the data obtained from a pair of ear-worn devices 16 to further improve the detection scheme. For instance, the data between the pair may be analyzed for similarities. Similar information across the ears during the breathing cycle may be considered as valid and used for breath detection, whereas all other data may be considered noise and not analyzed.

Figure 6:
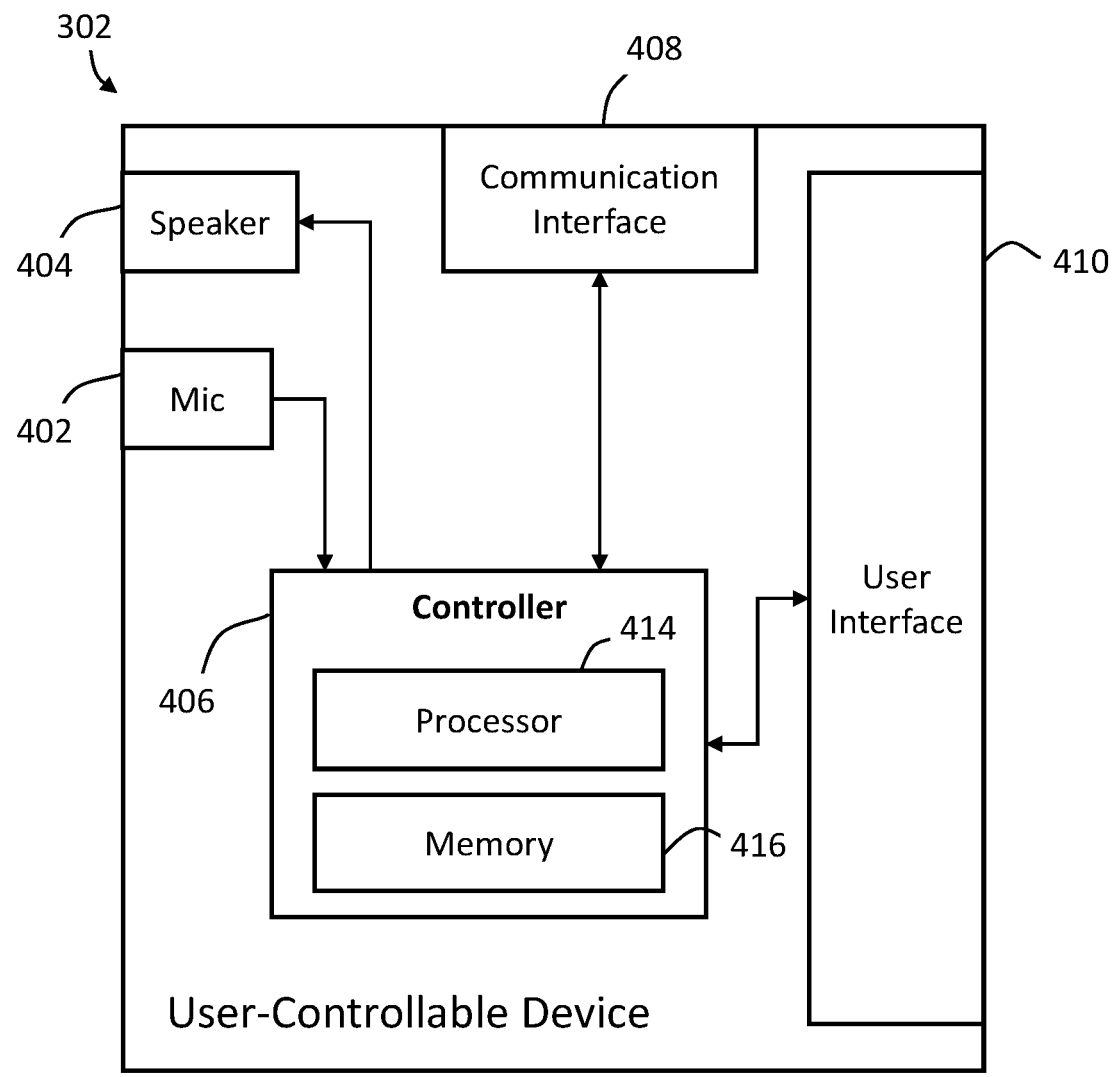
FIG. 6 shows a layout of one user-controllable device that may be used in the ambient acoustic environment of FIG. 5.

FIG. 6 shows one example of a layout for user-controllable device 302, which may run an application to provide the wearer with various functionality related to deep breathing exercise sessions. In the illustrated embodiment, user-controllable device 302 includes microphone 402, speaker 404, controller 406, communication interface 408, and user interface 410.

Controller 406 may include processor 414 and memory 416 for running an application and storing data related to deep breathing exercise sessions. Controller 406 may be operably coupled to communication interface 408 and user interface 410. In general, communication interface 408 is configured to connect to an ear-worn device, such as ear-worn device 16 (FIGS. 1-5). In some embodiments, controller 406 is configured to receive a request to initiate a deep breathing exercise based on user input at user interface 410. Controller 406 may be configured to connect to the ear-worn device to receive monitored breathing data based on user motion and optionally monitored ambient sound. Further, controller 406 may be configured to initiate an end to the deep breathing exercise.

User-controllable device 302 may be used to facilitate calibration of one or more sensors of ear-worn device 16, such as motion detector 210 (FIG. 4). In some embodiments, a calibration method may be carried out prior to the start of a deep breathing exercise session to determine a baseline for the motion detector. The calibration method may involve the wearer or may be carried out automatically in the background. In particular, the wearer may be provided with a series of onscreen, or streamed, instructions on user interface 410 that describe actions to carry out for calibration. The wearer may be asked to sit in a relaxed, seated position, while the ear-worn device calibrates a reference position.

In some embodiments, user interface 410 includes a display and a touchscreen or other user-selectable elements (e.g., buttons). In general, user interface 410 is configured to receive user input from the wearer and to provide information to the wearer. In general, the goal of the deep breathing exercise session may be to reduce the breathing rate, for example, below a threshold level. In some embodiments, controller 406 is configured to receive user input from user interface 410 including at least one of: a breathing exercise duration, a breathing rate starting goal, and a breathing rate end goal. In some embodiments, controller 406 is configured to command user interface 410 to display at least one of: a measured breathing rate, a breathing rate goal, guidance through the monitored deep breathing, and instructions for calibrating the ear-worn device.

Further, during the deep breathing exercise session, the wearer may be provided with guidance during deep breathing exercise, for example, with user interface 410 of user-controllable device 302 or with ear-worn device 16. In some embodiments, breathing rate guidance may be provided to the user based on a breathing rate goal. In some embodiments, deep breathing guidance is based on whether an inhalation, an exhalation, or a holding of the wearer's breath is detected. One or more of these parameters may be selected by the wearer, predetermined, or calculated, for example, by user-controllable device 302 or ear-worn device 16.

In some embodiments, the wearer may define a guided breathing session with user-controllable device 302. For example, the wearer may set a duration for the session as 10 minutes long. The breathing rate at the start of the session may be set by the wearer to 20 breaths per minute (BPM), and the breathing rate towards the end of the session may be set to a lower number such as 15 BPM. An application running on user-controllable device 302 may prompt the wearer for these parameters with user interface 410. User-controllable device 302 may perform a series of calculations to determine the rate of decrease in BPM to achieve the end goal that was set by the wearer. The application may use existing pre-determined calculations to determine the rate of decrease. In some embodiments, the application may use a linear or a log function to calculate the rate at which BPM may be decreased in order to achieve the goal at the end of the session. User-controllable device 302 may display in a graphical form, or otherwise, on user interface 410 the rate of BPM, so that the wearer is aware of their progress during the session.

In some embodiments, deep breathing data based on monitoring deep breathing over time may be logged and stored on memory 416 of user-controllable device 302 or memory 216 of ear-worn device 16. For example, the application running on user-controllable device 302 may also data-log various information for each session, so that the wearer is able to monitor their progress over time.

Progress data may be based on monitored breathing data, which may be logged, and may be provided to the wearer with user interface 410 of user-controllable device 302 or with ear-worn device 16. The progress data may include at least one of: results of a comparison of the deep breathing data and a deep breathing goal, merit badges received, and reminders to perform deep breathing exercises. Merit badges may be awarded to the user for achieving a particular deep breathing goal or series of goals. The progress data may also be stored on memory 416 of user-controllable device 302 or memory 216 of ear-worn device 16. In some embodiments, communication interface 408 is configured to connect to the internet to share progress data with others.

The wearer may also have the capability of sharing progress with persons of their choosing (e.g., friends) via various means, for instance through social media. The wearer may also be presented with the average information for persons in their age group for comparison.

The wearer may be presented with a series of merit badges when pre-determined goals, either available as options or set by the user, are achieved. A reminder management system may also be incorporated that sends out notifications to the user if desired. These functionalities may be carried out, for example, by one or both of the user-controllable device 302 or ear-worn device 16.

Figure 7:
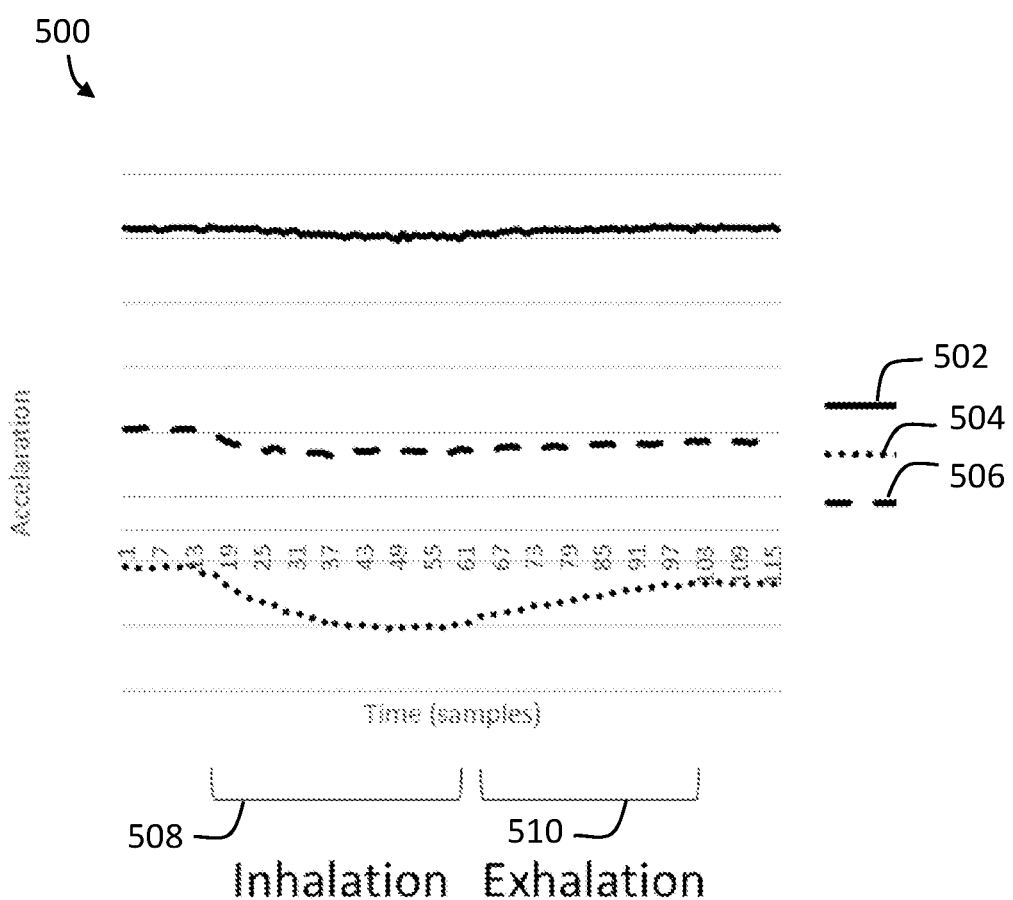
FIG. 7 shows a plot of acceleration versus time that may be used to detect breathing patterns.

FIG. 7 shows plot 500 of one example of data including acceleration versus samples in time from a motion detector, such as motion detector 210 (FIG. 4), in particular a 3-axis accelerometer, that may be used to detect breathing patterns. Acceleration may be measured, for example, in milli-g. Plot 500 shows first signal 502, second signal 504, and third signal 506 provided by a 3-axis accelerometer, which correspond to an X-axis, Y-axis, and Z-axis, respectively. Inhalation and exhalation may be detected using one or more signals 502, 504, 506. As illustrated, inhalation 508 may be detected in response to a decrease in second signal 504 (Y-axis), and exhalation 510 may be detected in response to an increase in second signal 504.

Figure 8:
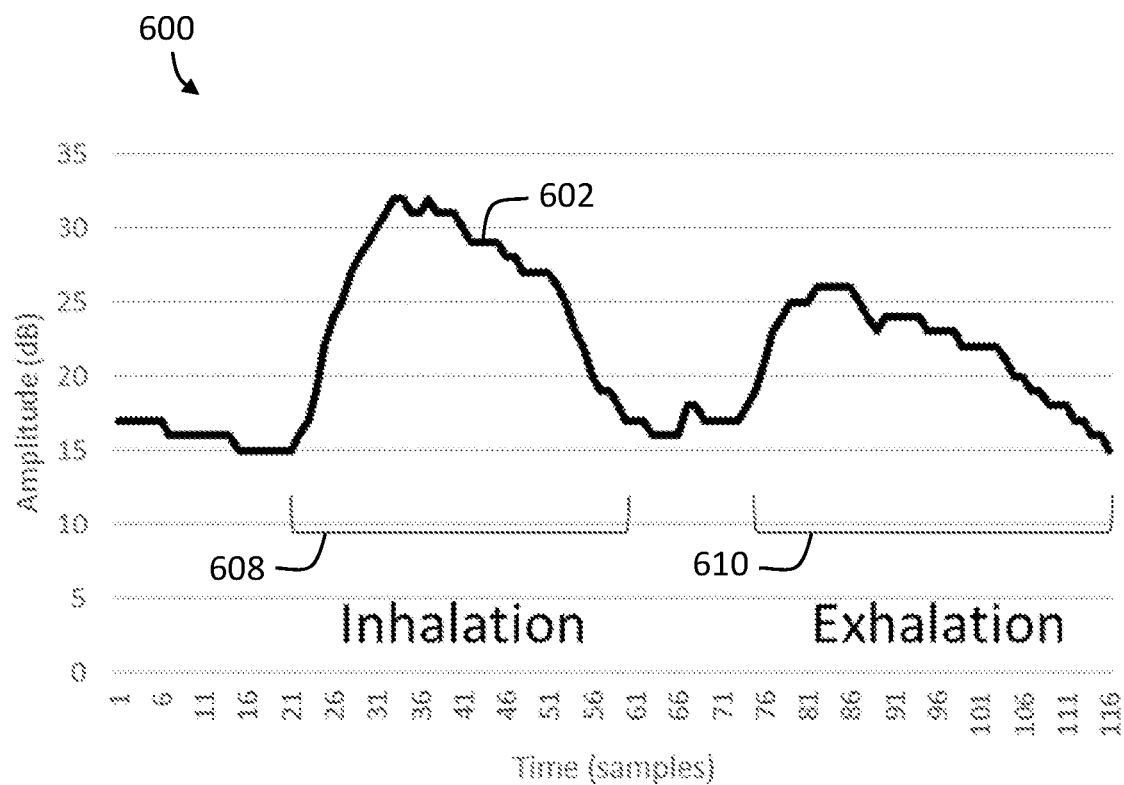
FIG. 8 shows a plot of sound level versus time that may be used to detect breathing patterns.

FIG. 8 shows plot 600 of one example of sound amplitude versus samples in time from a microphone, such as microphone 202 (FIG. 4) or microphone 402 (FIG. 6), that may be used to detect breathing patterns. Sound amplitude may be measured, for example in decibels. Plot 600 shows signal 602. As illustrated, inhalation 608 may be detected as a peak in signal 602, or increase and decrease, and exhalation 610 may be detected as a subsequent peak in signal 602. The peak of inhalation 608 may have a greater amplitude than the peak of exhalation 610.

Figure 9:
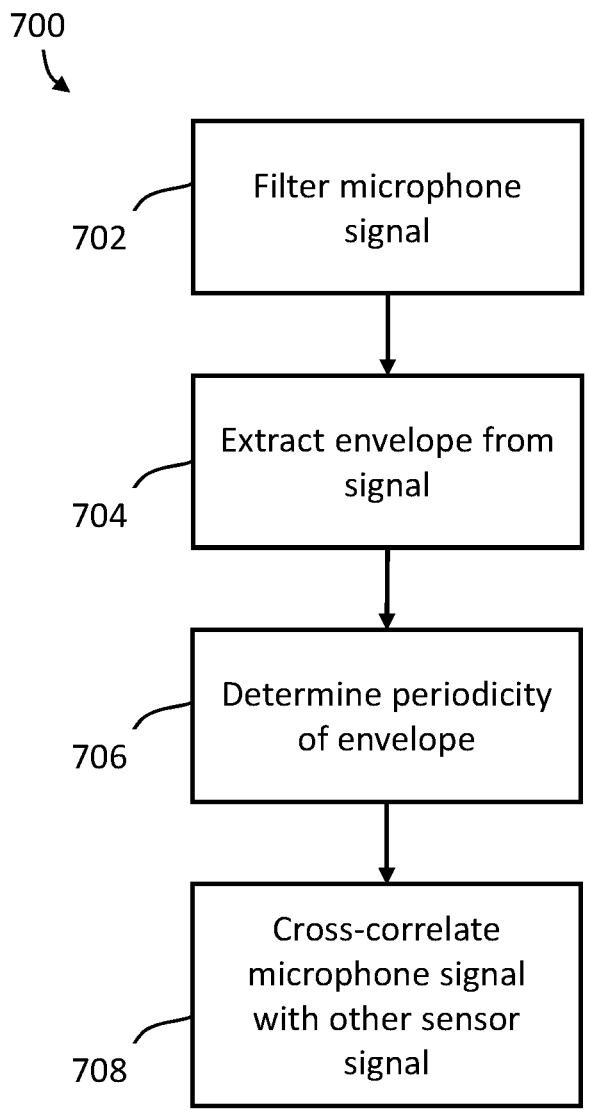
FIG. 9 shows one method for using a microphone signal to detect breathing patterns.

FIG. 9 shows one example of a method for processing a microphone signal from a microphone, such as microphone 202 (FIG. 4) or microphone 402 (FIG. 6), to facilitate breathing pattern detection. As illustrated, method 700 includes passing a microphone signal through a filter 702. The filter may be a low-pass, high-pass, or bandpass filter. Low-level noise may be removed by the filter.

Method 700 may continue and extract an envelope from the microphone signal 704, for example, after filtering. Envelope extraction may produce a smooth response signal, which may be used to infer a peak, trough, and period of any waveform in the signal. Existing envelope extraction techniques may be applied, such as the Hilbert transform or a low-pass filtering of absolute values. Examples of techniques for extracting envelopes are described, for example, in Potamianos, Alexandros, and Petros Maragos. "A comparison of the energy operator and the Hilbert transform approach to signal and speech demodulation." Signal processing 37.1 (1994): 95-120, and Schloss, W. Andrew. "On the Automatic Transcription of Percussive Music—From Acoustic Signal to High-Level Analysis." *Stanford University, Ph.D. Thesis* (1985), and Hartmann, William M. *Signals, Sound, and Sensation*. Springer-Verlag-AIP Press, 1997, which are incorporated by reference herein.

Peak detection may be performed on the envelope, for example, by identifying the maximum amplitude within a specified time frame. In some embodiments where only acoustic data is used, detection of inhalation and exhalation phases may be carried out using extraction of both time- and frequency-domain features that are used in classification techniques, such as voice activity detection, Mel-frequency cepstral coefficients, power level, zero-crossing rate, and so on. Examples of techniques that may be used to detect inhalation and exhalation phases are described, for example, in Yahya, Omar, and Miad Faezipour. "Automatic detection and classification of acoustic breathing cycles." *American Society for Engineering Education (ASEE Zone 1), 2014 Zone 1 Conference of the IEEE,* 2014, and Abushakra, Ahmad, and Miad Faezipour. "Acoustic signal classification of breathing movements to virtually aid breath regulation." *IEEE Journal of Biomedical and Health Informatics* 17.2 (2013): 493-500, which are incorporated by reference herein.

In some embodiments, classical or more sophisticated classification techniques using Gaussian Mixture Models, Support Vector Machines, and the like can be used to train a classifier to automatically detect various breathing phases in real-time.

In various embodiments, acoustic information could be used in combination with motion detector data to identify inhalation and exhalation phases. As an example, decrease in amplitude measured by a motion detector may correspond to a peak in signal measured by the acoustic data and may be classified as an inhalation event.

Method 700 may continue and determine a periodicity of the microphone signal 706, for example, after extracting the envelope to produce a smooth response signal. Auto-correlation functions may be used to determine the periodicity. For example, a breathing rate may be estimated as the inverse of the lag corresponding to the first, largest peak in the autocorrelation function of the microphone signal.

Method 700 may continue and cross-correlate the microphone signal from signals of other sensors 708, for example, after determining the periodicity. Cross-correlation functions may be used between the microphone signal and, for example different types of sensors (e.g., motion detector and other microphones) to obtain a measure of similarity across different signal domains, which may improve accuracy or precision of breathing-rate estimate.

In one example of cross-correlating information from various sensors, a motion detector, such as an inertial measurement unit (IMU), may be used to detect motion and generate a breath-related signal representing the motion, in which a slow deviation from baseline may indicate a breath cycle (e.g., including inhalation followed by exhalation) (see FIG. 7). An acoustic sensor of the microphone may be used to generate acoustic signal, in which an inhalation followed by an exhalation may give rise to two consecutive increases and decreases in amplitude (see FIG. 8). Information from the motion detector may be used to determine a breath cycle, while information from the microphone may provide finer granularity for the inhalation and exhalation cycles. In embodiments where acoustic information is not available, the peak and trough of the data obtained from the motion detector may be used instead to estimate inhalation and exhalation cycles.

Figure 10:
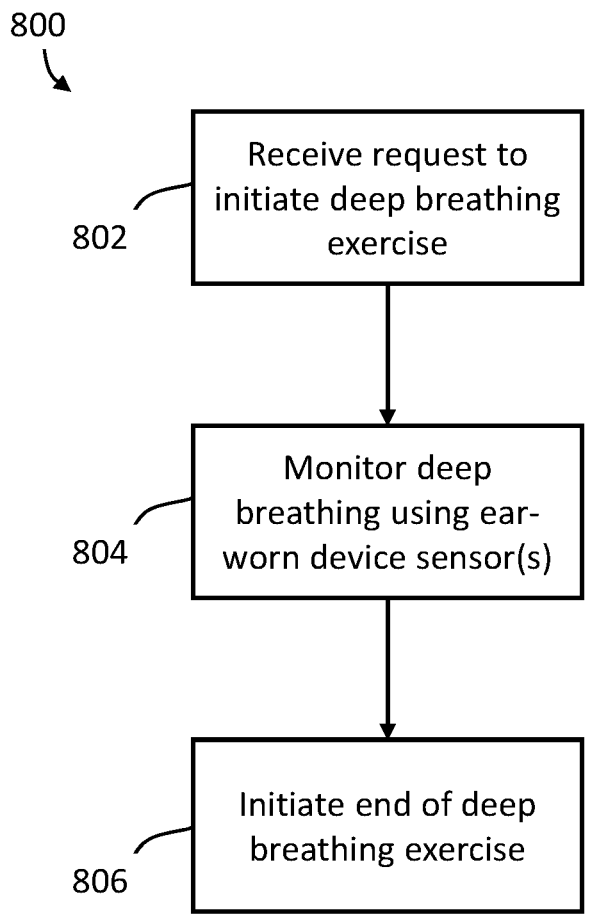
FIG. 10 shows one method for managing deep breathing sessions.

FIG. 10 shows a method for managing a deep breathing exercise session using an ear-worn device, such as ear-worn device 16 (FIGS. 1-5), and optionally a user-controllable device, such as user-controllable device 302 (FIGS. 5-6). In general, breath detection by ear-worn device 16 may not always be active. As illustrated, method 800 includes receiving a request to initiate a deep breathing exercise 802. The request may be made by a user or wearer of the ear-worn device or user-controllable device. The request may be made by the wearer to ear-worn device or user-controllable device, for example, using a touchscreen or voice command. Breath detection may be activated when the breathing session is initialized, which may conserve battery usage in both the ear-worn device and the user-controllable device for other types of processing.

Method 800 may continue and monitor deep breathing using one or more sensors of ear-worn device 804, for example, in response to initiating the deep breathing exercise. The one or more sensors may include at least one of a motion detector, a microphone, a heart rate sensor, and an electrophysiological sensor. In some embodiments, once the session initializes, the wearer may be guided through a series of deep breathing exercises that may be voice guided. Voice guidance in this context may be controlled by the application on the user-controllable device that helps the user focus on the breathing task. The voice guidance may be determined based on a series of parameters that the wearer defines. Some of these parameters may include the duration of the breathing session, the breathing rate at the start of the session, the breathing rate at the end of the session, inhalation rate, exhalation rate, and a hold duration.

During the guided session, voice-guidance may be automatically adjusted according to the rate of breaths defined. For example, the phrase "you're doing a good job" may be played through the ear-worn device or through the user-controllable device if the wearer's breathing rate moves closer to achieving a pre-determined breathing-rate goal.

In some embodiments, voice playback may be played in response to a relative to the rate of BPM determined by pre-defined set of logic. For example, the duration of the voice playback may be regulated by a duration for inhalation and exhalation set by the user. If exhalation is set for 5 seconds, a playback phrase such as "good job" may be used. If a longer exhalation time is set, such as 8 seconds, then a longer phrase such as "now exhale slowly," may be used instead. Alternatively, a shorter phrase may be used that is played closer to the end of the exhalation.

Voice guidance may be determined based on the breathing pattern of the user that are defined by a set of parameters. For example, phrases associated with inhalations may be played when inhalation is carried out and not during exhalations. Real-time analyses and feedback from ear-worn devices may be used to let the application on the user-controllable device know when the user is inhaling, exhaling, or holding their breath.

In some embodiments, audio feedback in the form of voice guidance or non-voice sounds may be delivered directly through the ear-worn device (e.g., hearing aid or other device). In some embodiments, the audio feedback may be delivered by another device (e.g., smartphone or Bluetooth device).

Further, method 800 may continue and initiate an end of the deep breathing exercise 806. In some embodiments, the end of the deep breathing exercise is initiated automatically after a predetermined period of time. In some embodiments, the end of the deep breathing exercise may be initiated by wearer input. Further, in some embodiments, the end of the deep breathing exercise may be initiated in response to achieving a deep breathing goal.

Figure 11:
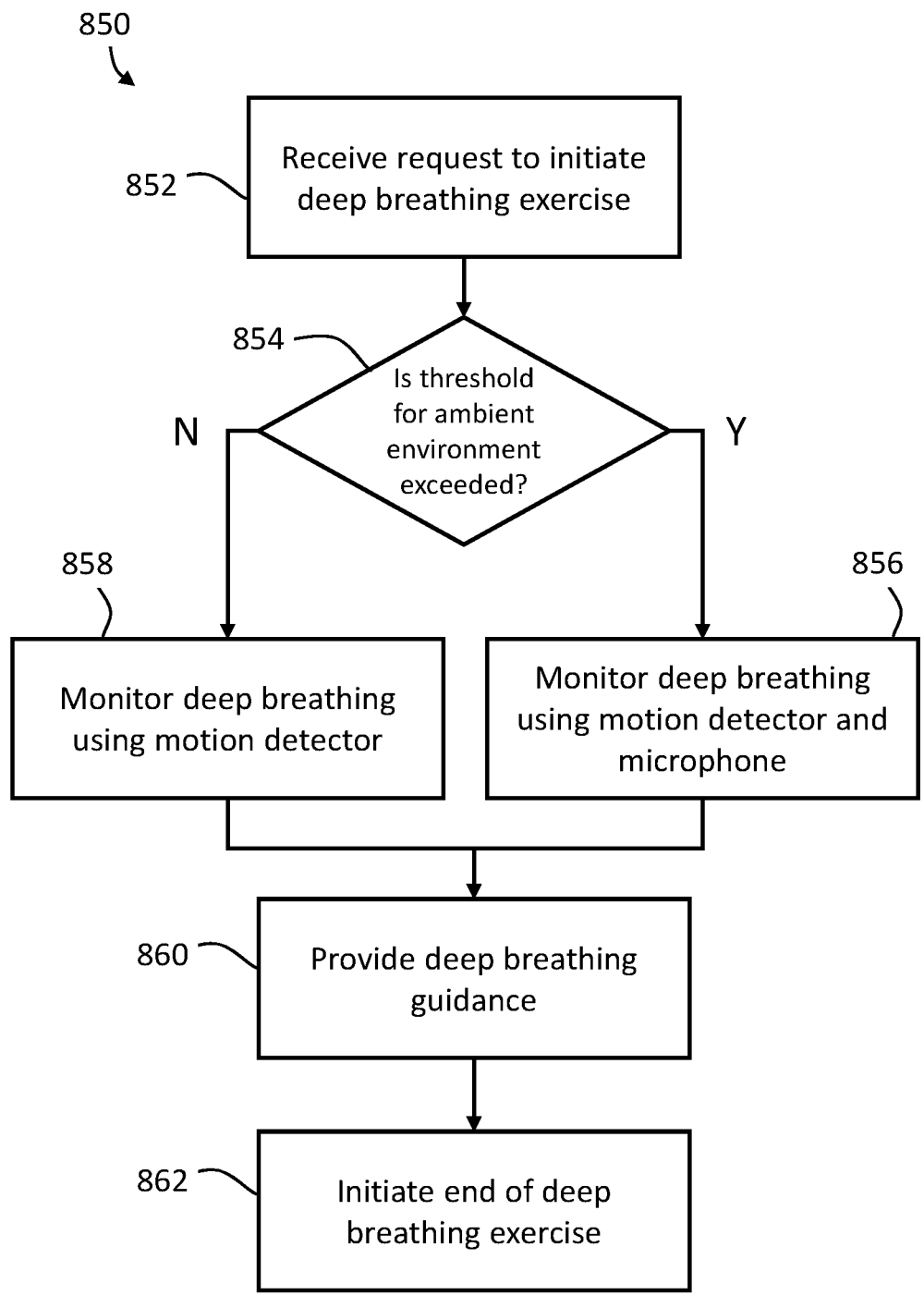
FIG. 11 shows one specific example of the method of FIG. 10.

FIG. 11 shows one example of method 850 for managing a deep breathing exercise session using an ear-worn device, such as ear-worn device 16 (FIGS. 1-5), and optionally a user-controllable device, such as user-controllable device 302 (FIGS. 5-6). As illustrated, method 850 includes receiving a request to initiate a deep breathing exercise 852.

Method 850 may also include determining whether a threshold for the ambient acoustic environment is exceeded 854, for example, determining whether a breathing pattern is detectable in an ambient acoustic environment such that inhalation and exhalation signatures are detectable. In some embodiments, one or more microphones of the ear-worn device or the user-controllable device may be used to measure sound levels of the ambient environment. If certain conditions are met regarding the sound levels, the breathing pattern may be determined as detectable. For example, there may be a sufficiently low amount of overall noise, or amount of noise in a particular frequency band, below a threshold value.

In some embodiments, checking conditions to determine whether a breathing pattern is detectable may be performed, for example, at the start of a deep breathing session. In other embodiments, the check may occur automatically in the background.

If the breathing pattern is detectable, when the acoustic information in the microphone signal is robust, for example, method 850 may include monitoring deep breathing using the motion detector and the microphone 856. In other words, monitored breathing data may be based on monitored user motion and monitored ambient sound in response to the breathing pattern being detectable.

If the breathing pattern is not detectable, method 850 may include monitoring deep breathing using the motion detector 858, and may not use a microphone signal. In other words, monitored breathing data may be provided without using monitored ambient sound in response to the breathing pattern not being detectable. For example, when ambient sounds are determined to be too loud, the use of the microphones may be nulled, and the detection scheme may use only the onboard motion detectors.

In some embodiments, the wearer may be advised to seek out a quiet place to carry out the session or may be asked to be stationary. Deep breathing exercises are typically carried out when the user is stationary, which may facilitate the accuracy of breath detection when using audio or motion signals.

Method 850 may continue and provide deep breathing guidance 860. Further, method 850 may continue and initiate an end of the deep breathing exercise 862.

Figure 12:
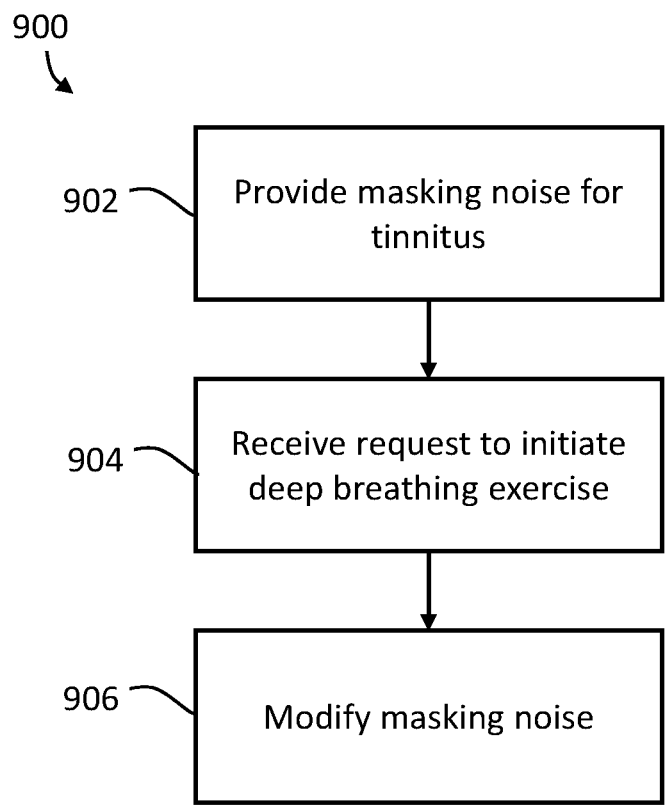
FIG. 12 shows one method for managing deep breathing sessions for tinnitus.

FIG. 12 shows a method for managing a deep breathing exercise session for tinnitus. A masking noise may be provided during at least part of a deep breathing exercise. As illustrated, method 900 may include providing a masking noise for tinnitus 902. In some embodiments, the tinnitus masking noise may be presented by the ear-worn device before the start of the sessions. Method 900 may include receiving a request to initiate the deep breathing exercise 904. In some embodiments, the tinnitus masking noise may be initiated before, during, or with (e.g., at the same time as) the deep breathing exercise.

Method 900 may include modulating the tinnitus masking noise heard 906, for example, in response to a detected breathing pattern (e.g., based on breathing rate). Tinnitus masking noise in this context may encompass any sound that may be used to provide relief from tinnitus, such as white noise or a recorded audio file. One or more parameters may be manipulated to modulate the tinnitus noise, such as a sound level (e.g., decibel level or sound amplitude), a frequency response, a modulation rate (e.g., for amplitude or frequency), a type of masking noise, and so on.

In one example, the modulation rate may be synchronized with the breathing rate such that inhalations would result in the tinnitus masking noise level to increase slightly, and then subsequently decrease on exhalation, or vice versa. In another example, the frequency of the tinnitus masking noise may be manipulated such that inhalations would cause a shift in the frequency response for more higher frequency emphasis, and exhalations would result in more lower frequency emphasis, or vice versa.

Thus, various embodiments of the EAR-WORN DEVICES WITH DEEP BREATHING ASSISTANCE are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure.

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a smartphone may be operatively coupled to the internet to send or receive data).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of" "consisting of," and the like are subsumed in "comprising," and the like.

The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. A method for guiding deep breathing, comprising:
   receiving a request from a user to initiate a deep breathing exercise on a user-controlled device;
   monitoring deep breathing using two or more sensors on an ear-worn device in response to initiating the deep breathing exercise, wherein the two or more sensors include a motion detector and at least one of a microphone, a heart rate sensor, and an electrophysiological sensor, and the monitoring comprises determining inhalation and exhalation cycles indicative of deep breathing of the user based on periodicity of signals produced by the two or more sensors;
   providing feedback to the user to modulate breathing in response to the monitored deep breathing; and
   initiating an end to the deep breathing exercise, wherein the deep breathing exercise mitigates a sleep disorder of the user.

2. The method of claim 1, wherein the deep breathing exercise comprises treating tinnitus of the user to mitigate the sleep disorder.

3. The method of claim 1, wherein the deep breathing exercise comprises providing a masking noise during at least part of the deep breathing exercise for treating tinnitus of the user to mitigate the sleep disorder.

4. The method of claim 3, further comprising modifying the masking noise in response to a detected breathing pattern.

5. The method of claim 4, wherein at least one parameter of the masking noise modified in response to the detected breathing pattern comprises at least one of a sound level, a frequency response, a modulation rate for amplitude, a modulation rate for frequency, and a type of masking noise.

6. The method of claim 1, further comprising:
   determining whether a breathing pattern is detectable in an ambient acoustic environment using a microphone of the ear-worn device or of the user-controlled device; and
   monitoring deep breathing using the motion detector and the microphone of the ear-worn device or of the user-controlled device in response to the breathing pattern being detectable.

7. The method of claim 1, further comprising initiating the end to the deep breathing exercise after a predetermined period of time, in response to wearer input, or in response to achieving a deep breathing goal.

8. The method of claim 1, further comprising calibrating the motion detector using a pre-determined baseline condition.

9. The method of claim 1, further comprising:
   logging deep breathing data based on the monitored deep breathing over time; and
   providing progress data based on the logged deep breathing data to the user with the user-controlled device or the ear-worn device.

10. The method of claim 1, further comprising:
    providing deep breathing guidance during the deep breathing exercise to the user with the user-controlled device or the ear-worn device, wherein:
    the breathing rate guidance provided to the user is based on a breathing rate goal; and
    content of the deep breathing guidance is based on whether an inhalation, an exhalation, or a holding of the breath is detected.

11. An ear-worn device, comprising:
    a housing configured to be worn by a user in or proximate to an ear of the user;
    a motion detector disposed in the housing and configured to monitor user motion;
    a microphone disposed in the housing and configured to monitor ambient sound;
    a communication interface disposed in the housing and configured to communicate with a user-controlled device;
    a controller comprising a processor disposed in the housing and operably coupled to the motion detector, the microphone, and the communication interface, the controller configured to:
    receive a request to initiate a deep breathing exercise from the user-controlled device;
    monitor user motion and ambient sound in response to receiving the request, wherein the monitoring comprises determining inhalation and exhalation cycles indicative of deep breathing of the user based on periodicity of the monitored user motion and ambient sound;
    provide monitored breathing data based on the monitored user motion and ambient sound; and
    provide feedback to the user of the ear-worn device to modulate breathing in response to the monitored breathing data, wherein the deep breathing exercise mitigates a sleep disorder of the user.

12. The device of claim 11, wherein the controller is configured to provide a masking noise during at least part of the deep breathing exercise for treating tinnitus of the user to mitigate the sleep disorder.

13. The device of claim 11, wherein the controller is configured to:
provide a masking noise for treating tinnitus of the user to mitigate the sleep disorder; and
modify the masking noise in response to a detected breathing pattern.

14. The device of claim 13, wherein at least one parameter of the masking noise modified by the controller in response to the detected breathing pattern comprises at least one of a sound level, a frequency response, a modulation rate for amplitude, a modulation rate for frequency, and a type of masking noise.

15. The device of claim 11, wherein the controller is configured to:
determine whether a breathing pattern is detectable in an ambient acoustic environment using a microphone of the ear-worn device or of the user-controlled device; and
provide monitored breathing data based on monitored user motion and monitored ambient sound in response to the breathing pattern being detectable.

16. The device of claim 15, wherein the controller is configured to provide monitored breathing data without using monitored ambient sound in response to the breathing pattern not being detectable.

17. The device of claim 11, wherein the motion detector comprises at least one of an accelerometer and a gyroscope.

18. The device of claim 11, wherein the controller is configured to calibrate the motion detector using a pre-determined baseline condition.

19. The device of claim 11, wherein the controller is configured to:
log deep breathing data based on the monitored deep breathing over time; and
provide progress data based on the logged deep breathing data to the user with the user-controlled device or the ear-worn device.

20. The device of claim 11, wherein:
the controller is configured to provide deep breathing guidance during the deep breathing exercise to the user with the user-controlled device or the ear-worn device;
the breathing rate guidance provided to the user is based on a breathing rate goal; and
content of the deep breathing guidance is based on whether an inhalation, an exhalation, or a holding of the breath is detected.

21. A user-controllable device, comprising:
a user interface comprising a display and configured to receive user input;
a communication interface configured to connect to an ear-worn device;
a controller comprising a processor operably coupled to the user interface and the communication interface, the controller configured to:
receive a request to initiate a deep breathing exercise based on user input at the user interface;
connect to the ear-worn device to receive monitored breathing data derived from monitoring user motion and ambient sound, wherein the monitoring comprises determining inhalation and exhalation cycles indicative of deep breathing of the user based on periodicity of the monitored user motion and ambient sound;
provide feedback to the user to modulate breathing in response to the monitored breathing data; and
initiate an end to the deep breathing exercise, wherein the deep breathing exercise mitigates a sleep disorder of the user.

22. The device of claim 21, wherein the controller is configured to provide a masking noise during at least part of the deep breathing exercise for treating tinnitus of the user to mitigate the sleep disorder.

23. The device of claim 21, wherein the controller is configured to:
provide a masking noise for treating tinnitus of the user to mitigate the sleep disorder; and
modify the masking noise in response to a detected breathing pattern.

24. The device of claim 23, wherein at least one parameter of the masking noise modified by the controller in response to the detected breathing pattern comprises at least one of a sound level, a frequency response, a modulation rate for amplitude, a modulation rate for frequency, and a type of masking noise.

* * * * *